United States Patent [19]
Osborn et al.

[11] Patent Number: 6,010,979
[45] Date of Patent: Jan. 4, 2000

[54] HERBICIDAL COMPOSITION

[75] Inventors: Martin Keith Osborn, Wokingham; Michael John Bean, Bracknell; Philip Simon Wikeley, Loughborough, all of United Kingdom

[73] Assignee: Zeneca Limited, United Kingdom

[21] Appl. No.: 09/068,378

[22] PCT Filed: Dec. 19, 1996

[86] PCT No.: PCT/GB96/03417

§ 371 Date: May 8, 1998

§ 102(e) Date: May 8, 1998

[87] PCT Pub. No.: WO97/23131

PCT Pub. Date: Jul. 3, 1997

[30] Foreign Application Priority Data

Dec. 22, 1995 [GB] United Kingdom ................... 9526441

[51] Int. Cl.[7] ............................. A01N 25/30; A01N 57/02
[52] U.S. Cl. .......................................................... 504/206
[58] Field of Search ............................................. 504/206

[56] References Cited

U.S. PATENT DOCUMENTS

| | | | |
|---|---|---|---|
| 4,264,478 | 4/1981 | Seldner | 252/522 R |
| 4,528,106 | 7/1985 | Grolitzer | 252/8.55 D |
| 5,258,359 | 11/1993 | Kassebaum et al. | 504/206 |
| 5,612,285 | 3/1997 | Arnold | 504/206 |
| 5,888,934 | 3/1999 | Townson et al. | 504/206 |

FOREIGN PATENT DOCUMENTS

| | | |
|---|---|---|
| 0 432 646 A2 | 6/1991 | European Pat. Off. . |
| 0 526 443 A1 | 2/1993 | European Pat. Off. . |
| 0 582 561 A1 | 2/1994 | European Pat. Off. . |
| 93/22917 | 11/1993 | WIPO . |
| 95/03881 | 2/1995 | WIPO . |
| 95/16351 | 6/1995 | WIPO . |
| 96/00010 | 1/1996 | WIPO . |
| 96/34078 | 10/1996 | WIPO . |

*Primary Examiner*—S. Mark Clardy
*Attorney, Agent, or Firm*—David P. LeCroy

[57] ABSTRACT

New and useful herbicidal compositions comprising N-phosphonomethylglycineor an agriculturally acceptable salt thereof, an ethoxylated alkyl glycoside surfactant, and an ethoxylated alcohol are provided.

11 Claims, No Drawings

HERBICIDAL COMPOSITION

This application has been filed under 35 USC 371 as the national stage of international application PCT/GB96/03147, filed Dec. 19, 1996.

This invention relates to a herbicidal composition and in particular to a glyphosate composition.

The term "glyphosate composition" is used herein to mean a herbicidal composition comprising an active ingredient N-phosphonomethylglycine or a herbicidally acceptable salt thereof.

Herbicidally active glyphosate compositions are well known and are commercially available in the form of the trimethylsulphonium, isopropylamine and other salts. Such compositions are generally applied to unwanted vegetation in the form of an aqueous formulation containing a variety of adjuvants including for example wetters or other surface-active agents, anti-freeze agents, dyes, dispersants, rheological agents, anti-foam agents and humectants. The activity of the glyphosate composition may be improved considerably by the careful choice of additives. The literature contains many hundreds of examples of different glyphosate formulations exhibiting a variety of properties and designed for a variety of purposes.

Glyphosate compositions are very effective in killing unwanted weeds to which they are applied. However the uptake of the glyphosate composition by the plant leaf surface is relatively slow. In consequence the composition may be washed off the leaf surface and the herbicidal effectiveness may be reduced or even lost if rain falls shortly after application of the composition (for example within 6 hours of application). This is a particular problem for example in tropical climates in which it is difficult to predict the occurrence of heavy rain showers. Glyphosate compositions have been produced which are claimed to give improved rainfastness, but the topic is poorly understood and the physical parameters involved are highly complex and may vary from species to species. It may for example be appropriate to provide a composition which generally improves rainfastness for most species but is relatively ineffective on particular individual species. One approach which has been studied is to seek to improve the rate of uptake of the glyphosate composition into the leaf surface with a view to minimising the susceptibility to rain. Such improved uptake is often only achieved however at the expense of localised tissue damage and reduced translocation. It is clearly important that improved rainfastness is not associated with a significant reduction in herbicidal activity in the absence of rain. It is therefore desired to provide a glyphosate composition combining good activity in the absence of rain with effective rainfastness.

The present invention seeks to provide herbicidally effective compositions having improved rainfastness, by which is meant that compositions of the present invention generally reduce the overall loss in herbicidal effectiveness resulting from a fall of rain within for example from 1 to 6 hours after application of the composition. Compositions of the present invention may also show enhanced activity as compared with known glyphosate compositions and advantage as compared with known compositions may be found in either one or in both of these effects.

According to the present invention there is provided a glyphosate composition comprising (i) N-phosphonomethylglycine or an agriculturally acceptable salt thereof, (ii) a alkylglycoside surfactant of formula (I):

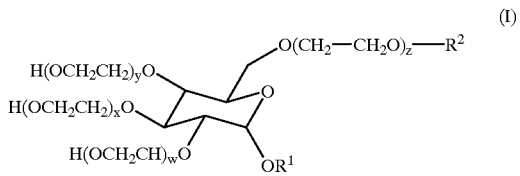

wherein $R^1$ represents a C1 to C8 alkyl group, the sum of w+x+y+z is from 4 to 40 and $R^2$ is hydrogen or a C1 to C6 alkyl group or a group of formula —$R^3$—$N^{(+)}R^4R^5R^6$ $X^-$ wherein $R^3$ is a C1 to C6 alkylene group optionally substituted with hydroxy, $R^4$, $R^5$ and $R^6$ are each alkyl groups wherein the total number of carbon atoms in $R^4$, $R^5$ and $R^6$ is from 6 to 25 and $X^-$ is an agrochemically acceptable anion and (iii) an ethoxylated alcohol.

$R^1$ preferably represents a C1 to C4 alkyl group for example methyl. The total number of ethylene oxide chains is represented by the sun of w+x+y+z. The sum of w+x+y+z is preferably 4 to 25. Preferably, w, x, y and z are each separately at least 1. It will be appreciated that the sum w+x+y+z may vary as between individual molecules and may have a relatively wide distribution range in any given product. The value given is an average over the product as a whole.

When the substituent $R^2$ is the group:

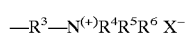

$X^-$ is suitably a halide anion such as chloride and $R^3$ is preferably an optionally hydroxy substituted propylene group such as:

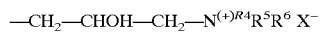

wherein $R^4$ and $R^5$ $R^6$ are alkyl groups having a total number of carbon atoms (i.e. a total of $R^4+R^5+R^6$) of from 6 to 25. In formula (I) and in the above group, $R^4$ and $R^5$ are preferably short chain alkyl groups, for example, methyl or ethyl groups and the additional chain length preferably resides in $R^6$.

As examples of suitable ethoxylated alkylglucosides which may be used in the present invention may be mentioned the compound available under the trade name GLUCAM E-10 and E-20 of structure (II) wherein w+x+y+z represents 10 for GLUCAM E-10 AND 20 FOR GLUCAM E-20, and the compound available under the trade name GLUCQUAT 125 having the structure (III) wherein w+x+y+z represents 10. The product GLUCQUAT 125 is a 25% by weight solution of the above compound in water.

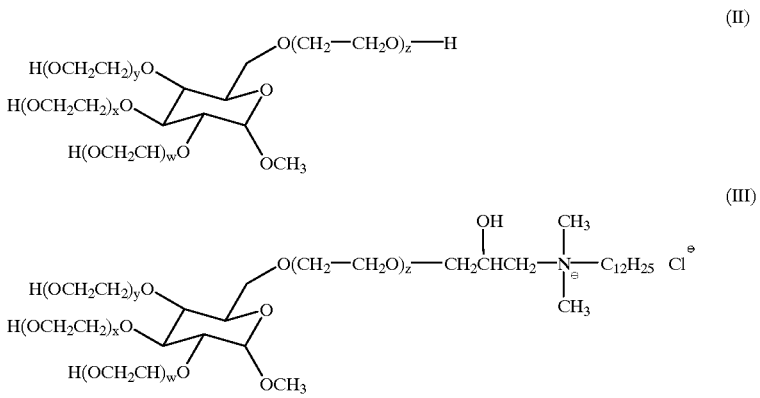

The ethoxylated alcohol is preferably a linear or branched chain saturated or unsaturated aliphatic or aromatic alcohol and may have one or more hydroxy groups. The ethoxylated alcohol is preferably obtained by ethoxylation of a linear or branched chain aliphatic mono alcohol having a chain length of from 8 to 20 carbon atoms or a mixture of such alcohols having an average chain length of from 8 to 20 and more preferably from 10 to 18 carbon atoms. An example of an ethoxylated alcohol for use in the present invention is that derived from a mixture of a linear alcohol containing 13 carbon atoms and an linear alcohol containing 15 carbon atoms. The ratio of the C13 alcohol to the C15 alcohol is typically from 30:70 to 70:30 and the mixture generally contains both linear and branched alcohols, for example, about 50% by weight of linear alcohols. An example of an ethoxylated aromatic alcohol is nonylphenol ethoxylate.

The mean degree of ethoxylation (mean molar ethylene oxide content) is preferably from 2 to 50 moles of ethylene oxide per mole of alcohol, and especially from 10 to 20 moles of ethylene oxide per mole of alcohol. The most efficacious degree of ethoxylation may vary somewhat depending upon the weed species being treated. It is therefore possible either to select the most efficacious mean degree of ethoxylation for a specific target weed or to seek an mean degree of ethoxylation which is efficacious over a broad range of species. In general we have found that effective treatment over a broad range of species is obtained when the mean degree of ethoxylation is from 11 to 18 moles of ethylene oxide per mole of alcohol. There may in some instances be an advantage in obtaining a broad species response by using a composition having a broad distribution of ethylene oxide content around the mean value. The appropriate mean ethylene oxide content may if desired be obtained by mixing two or more commercially available ethoxylated alcohols having various ethylene oxide contents in the appropriate ratio. This has the dual advantage of enabling a desired mean ethylene oxide content to be achieved precisely and also of ensuring that a broad distribution of ethylene oxide contents is present. Thus for example a mean ethylene oxide content of 15 moles of ethylene oxide per mole of alcohol may be achieved by mixing the commercially available ethoxylated alcohol SYNPERONIC A11 (SYNPERONIC is a trademark of IMPERIAL CHEMICAL INDUSTRIES PLC) which has a mean ethylene oxide content of 11 with SYNPERONIC A20 (which has a mean ethylene oxide content of 20) in the ratio 3 to 2.

A number of suitable ethoxylated alcohols are commercially available including for example the SYNPERONIC A series having a range of ethylene oxide contents (indicated by the number after the "A") and based on a $C_{13}$–$C_{15}$ alcohol containing about 50% by weight linear alcohol, the remainder being mainly mono-branched; CIRRASOL ALN-WF (a mixture of C16–C18 linear alcohols with a mean ethylene oxide content of 17); BRIJ 96 and 98 based on an unsaturated $C_{18}$ linear alcohol and having a mean ethylene oxide content of 10 and 20 respectively; and RENEX 30 based on a branched $C_{13}$ alcohol having a mean ethylene oxide content of 12.

The N-phosphonomethylglycine or agriculturally acceptable salt thereof is conveniently the trimethylsulphonium, isopropylamine, sodium, or ammonium salt, although N-phosphonomethylglycine itself or any agriculturally acceptable salt thereof is acceptable for incorporation in the composition of the present invention. It is preferred to use a water-soluble salt of N-phosphonomethylglycine.

The composition of the present invention may be a dilute aqueous herbicidal composition which is sold ready for immediate use or may be formulated as an aqueous herbicidal concentrate which is diluted prior to use. Alternatively, the components of the composition may be mixed together and diluted shortly before application.

Thus in one embodiment of the present invention there is provided an aqueous herbicidal concentrate which is sufficiently storage-stable for commercial use and which is diluted before use, usually with water. The term "herbicidal concentrate" covers a range of compositions from the relatively dilute which requires the addition of relatively little water to a more concentrated composition which has a high content of glyphosate and thus has advantages for handling and transportation. The preference for a concentrated glyphosate rainfast composition poses an additional problem which must be solved, since many adjuvants are incompatible with each other or with the active ingredient in concentrated compositions. By the term "concentrated" glyphosate composition is meant a composition having a concentration greater than 210 g/l for example greater than 220 g/l based on glyphosate acid. In the case of the trimethylsulphonium salt of glyphosate for example, this equates to a concentration of greater than 304 g/l and more particularly greater than about 319 g/l based on the salt.

In an alternative embodiment of the present invention the alkyl glucoside and the ethoxylated alcohol may be formulated together, optionally with other adjuvants such as an inorganic salt or one or more additional surfactants as described below, to form an adjuvant composition suitable for tank mixing with a glyphosate composition. The adjuvant composition is tank mixed prior to use, for example with a commercially available glyphosate composition. The glyphosate composition could be an aqueous formulation containing essentially only glyphosate or could itself contain suitable adjuvants.

Thus according to a further aspect of the present invention there is provided an adjuvant composition suitable for admixture with N-phosphonomethylglycine or an agriculturally acceptable salt thereof to form a composition according to the present invention which adjuvant composition comprises (i) an ethoxylated alkylglucoside surfactant and (ii) an ethoxylated alcohol and optionally (iii) an additional surfactant.

The proportion of ethoxylated alkylglucoside present in the herbicidal composition or in the adjuvant composition is preferably from 1 part by weight of ethoxylated alkylglucoside per 5 parts ethoxylated alcohol to 8 parts by weight of ethoxylated alkylglucoside per 1 part ethoxylated alcohol and most preferably from 0.5 parts by weight of ethoxylated alkylglucoside per 1 part ethoxylated alcohol to 8 parts by weight ethoxylated alkylglucoside per 1 part ethoxylated alcohol for example from 1 part by weight ethoxylated alkylglucoside per 1 part by weight ethoxylated alcohol to 8 parts by weight ethoxylated alkylglucoside per 1 by weight part ethoxylated alcohol. An especially preferred composition contains about equal proportions by weight of ethoxylated alkylglucoside and ethoxylated alcohol.

If the composition contains a relatively high proportion of ethoxylated alcohol it may be desirable to add an additional surfactant to enhance stability, especially if the composition is used in the form of an aqueous concentrate. A wide range of suitable additional surfactants will occur to those skilled in the art and those which have been found to enhance stability include cationic or nonionic surfactants containing an amine, ammonium or amine oxide group for example quaternary tetra-alkyl ammonium salt surfactants such as hexadecyl trimethyl ammonium chloride and primary or quaternary ethoxylated long-chain alkyl amines such as coco-anine, hydrogenated tallow amine each having a mean ethylene oxide content of from 2 to 20 when ethoxylated. In some instances, the additional surfactant may even provide an increase in the activity of the composition. Thus especially preferred additional surfactants are optionally ethoxylated quaternary ammonium salts having at least one long chain substituent containing from 10 to 20 carbon atoms and mean ethylene oxide content of from 0 to 5. Examples of suitable additional surfactants include hexadecyl trimethyl ammonium chloride, trimethyl tallowammonium chloride, trimethyl cocoammonium chloride and N-methyl cocoammonium chloride having a mean ethylene oxide content of 2.

The proportion of additional surfactant is preferably from 0 to 2 parts by weight per 1 part by weight of ethoxylated alcohol and more preferably about 1 part by weight per 1 part by weight of ethoxylated alcohol. Thus an especially preferred composition comprises a total adjuvant system comprising substantially equal proportions by weight of ethoxylated alkylglucoside, ethoxylated alcohol and additional surfactant.

The proportion by weight of the total adjuvant system (ethoxylated alkylglucoside, ethoxylated alcohol and any additional surfactant used) to the glyphosate salt in a concentrate composition is preferably from 3:1 to 1:3 and especially from 1:1 to 1:3. A ratio of about 1:2 is especially preferred. Higher proportions of adjuvant system may be used if desired in a tank mix or ready to use composition.

In some circumstances the activity of the present composition may be enhanced by the incorporation of a humectant.

Thus according to a further aspect of the present invention there is provided a glyphosate composition comprising (i) N-phosphonomethylglycine or an agriculturally acceptable salt thereof, (ii) an ethoxylated alkylglucoside surfactant, (iii) an ethoxylated linear or branched chain alcohol and (iv) a humectant.

Suitable humectants include glycerol, polyethylene glycol, sorbitol, ethylene glycol, propylene glycol and lactate salts such as sodium or ammonium lactate. For the compositions of the present invention we have found that glycerol, polyethylene glycol, sorbitol and sodium lactate are especially effective in enhancing activity. When polyethylene glycol is used as humectant, the molecular weight is preferably in the range 100 to 1200 and more particularly from 200 to 1000. The enhancement of activity provided by polyethylene glycol of a given molecular weight depends to some extent on the target weed species, but in general a low-molecular weight polyethylene glycol, for example a polyethylene glycol of molecular weight about 200, is preferred.

The humectant is most conveniently used in a tank mix composition or in a ready to use composition. The proportion is preferably from 1 part of glyphosate salt per 1 part humectant to 1 part glyphosate salt per 20 parts humectant.

The composition of the present invention may additionally include an inorganic ammonium salt such as ammonium sulphate as an activity-enhancing adjuvant. The proportion of ammonium sulphate (if used) is preferably from 1 part inorganic ammonium salt per 1 part glyphosate salt to 10 parts ammonium salt per 1 part glyphosate salt. The ammonium salt is most conveniently used in a tank mix composition or in a ready to use composition.

Compositions of the present invention are active against a broad range of weed species including monocotyledonous and dicotyledonous species. The compositions of the present invention are suitably applied directly to unwanted plants (post-emergence application).

Thus according to a further aspect of the present invention there is provided a process of severely damaging or killing unwanted plants, and more particularly a process of providing enhanced activity or enhanced rainfastness which comprises applying to the plants a herbicidally effective amount of a composition of the present invention.

Compositions of the present invention include both solid compositions, dilute compositions, which are ready for immediate use, and concentrated compositions, which require to be diluted before use, usually with water. Preferably the compositions contain from 0.01% to 90% by weight of the agriculturally acceptable salt of N-phosphonomethylglycine. Dilute compositions ready for use preferably contain from 0.01 to 2% of agriculturally acceptable salt of N-phosphonomethylglycine, while concentrated compositions may contain from 20 to 90% of agriculturally acceptable salt of N-phosphonomethylglycine, although from 20 to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution, suspension or dispersion of the active ingredients in water optionally containing a surface-active agent, or may comprise a solution or dispersion of the active ingredient in a waterimmiscible organic solvent which is dispersed as droplets in water. Preferred active ingredients of the composition of the present invention are water-soluble herbicides or are readily suspended in water and it is preferred to use aqueous compositions and concentrates. In particular, the trimethylsulphonium, isopropylamine, sodium and ammonium salts of glyphosate are all readily soluble in water.

The composition of the present invention may contain additional surface active agents, including for example surface active agents to increase the compatibility or stability of concentrated compositions as discussed above. Such surface-active agents may be of the cationic, anionic, or non-ionic or amphoteric type or mixtures thereof. The cationic agents are, for example, quaternary ammonium compounds (e.g. cetyltrimethylammonium bromide). Suitable anionic agents are soaps; salts of aliphatic mono ester of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropyinaphthalenesulphonic acid. Suitable non-ionic agents are the condensation products of ethylene oxide with fatty alcohols such as oleyl alcohol and cetyl alcohol, or with alkylphenols such as octyl- or nonyl-phenol (e.g. Agral 90) or octylcresol. Other non-ionic agents are the partial esters derived from long chain fatty acids and hexitol anhydrides, for example sorbitan monolaurate; the condensation products of the partial ester with ethylene oxide; the lecithins; and silicone surface active agents (water soluble or disperible surface active agents having a skeleton which comprises a siloxane chain e.g. Silwet L77). A suitable mixture in mineral oil is ATPLUS 411F.

The aqueous solutions or dispersions may be prepared by dissolving the active ingredients in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene, although as indicated above it is preferred to use an entirely aqueous system for compositions of the present invention.

The compositions for use in the form of aqueous solutions or dispersions are generally supplied in the form of a concentrate containing a high proportion of the active ingredients, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–70%, preferably 20–50%, by weight of the agriculturally acceptable salt of N-phosphonomethylglycine. Dilute preparations ready for use may contain varying amounts of the agriculturally acceptable salt of N-phosphonomethylglycine depending upon the intended purpose; amounts of 0.01% to 10.0% and preferably 0.1% to 2%, by weight of agriculturally acceptable salt of N-phosphonomethylglycine are normally used.

Other additives and adjuvants may also be present in compositions of the present invention. Examples include anti-freeze agents such as ethylene glycol and propylene glycol; dyes; dispersants; rheological agents; and anti-foam agents such as silicone based agents.

The rate of application of the composition of the invention will depend on a number of factors including, for example, the active ingredients chosen for use, the identity of the plants whose growth is to be inhibited and the formulations selected for use and whether the compound is to be applied for foliage or root uptake. As a general guide, however, an application rate of from 0.001 to 20 kilograms per hectare is suitable while from 0.025 to 10 kilograms per hectare may be preferred.

The compositions of the invention may also comprise one or more additional compounds which possess biological activity, for example herbicides, fungicides, insecticides (optionally with an insecticide synergist) and plant growth regulators.

The other herbicide may be any herbicide other than a glyphosate salt. It will generally be a herbicide having a complementary action in the particular application.

Examples of useful complementary herbicides include:

A. benzo-2,1,3-thiadiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, clopyralid, and their derivatives (eg. salts, esters and amides);

C. 1,3 dimethylpyrazole derivatives such as pyrazoxyfen, pyrazolate and benzofenap;

D. Dinitrophenols and their derivatives (eg. acetates) such as dinoterb, dinoseb and its ester, dinoseb acetate;

E. dinitroaniline herbicides such as dinitramine, trifluralin, ethalflurolin, pendimethalin, oryzalin;

F. arylurea herbicides such as diuron, flumeturon, metoxuron, neburon, isoproturon, chlorotoluron, chloroxuron, linuron, monolinuron, chlorobromuron, daimuron, methabenzthiazuron;

G. phenylcarbamoyloxyphenylcarbamates such as phenmedipham and desmedipham;

H. 2-phenylpyridazin-3-ones such as chloridazon and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, tri-allate, di-allate, esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, alachlor, propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, flurogly- cofen or salts or ester thereof, nitrofen, bifenox, aci- flurofen and salts and esters thereof, oxyfluorfen, fomesafen, chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxyidim, tralkoxydim, and clethodim;

U. sulfonyl urea herbicides such as chlorosulfuron, sulfometuron, metsulfuron and esters thereof; benzsulfuron and esters thereof such as DPX-M6313, chlorimuron and esters such as the ethyl ester thereof pirimisulfuron and esters such as the methyl ester thereof, 2-[3-(4-methoxy-6-methyl-1,3,5-triazin-zyl)-3-methylureidosulphonyl] benzoic acid esters such as the methyl ester thereof (DPX-LS300) and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glufosinate and its esters.

Y. organoarsenical herbicides such as monosodium methanearsonate (MSMA);

Z. herbicidal amide derivative such as napropamide, propyzamide, carbetamide, tebutam, bromobutide, isoxaben, naproanilide and naptalam;

AA. miscellaneous herbicides including ethofumesate, cinmethylin, difenzoquat and salts thereof such as the methyl sulphate salt, clomazone, oxadiazon, bromofenoxim, barban, tridiphane, flurochloridone, quinclorac, dithiopyr triketone herbicides and mefanacet;

BB. Examples of useful contact herbicides include:
bipyridylium herbicides such as those in which the active entity is paraquat and those in which the active entity is diquat;

* These compounds are preferably employed in combination with a safener such as dichlormid.

The compositions of the present invention may be supplied in pre-mixed form or may be tank mixed shortly before application.

The invention is illustrated by the following Examples in which all parts and percentages are by weight unless otherwise indicated. Treatment rates (indicated for example as g/ha) are expressed in terms of the weight of active ingredient.

EXAMPLE 1

This Example illustrates the herbicidal activity and rainfastness of compositions of the present invention.

A tank-mixed adjuvant system at a concentration of 0.25% w/v was added to aqueous solutions of the trimethylsulphonium salt of N-phosphonomethylglycine at four doses of 125 g/ha, 250 g/ha, 500 g/ha and 1000 g/ha respectively. Activity (damage to plants) was assessed a given number of days after treatment (depending on species, see Table I)) by comparison with untreated plants on a 0–100% scale, where 0% is no damage and 100% is complete kill. The rate required for 90% control (ED 90) against a given species was calculated from these data. It should be noted that the smaller the value of the ED 90 figure, the more active is the composition.

The adjuvant system contained equal parts by weight of an ethoxylated alkylglucoside of formula (III) above (commercially available as a 25% solution under the trademark GLUCQUAT 125) and a mixture of ethoxylated branched linear $C_{13}$–$C_{15}$ alcohols having ethylene oxide contents of 11 and 20 respectively (SYNPERONIC A11 and SYNPERONIC A20 in the ratio of 60 to 40) giving an overall mean ethylene oxide content of about 15. The ED 90 Data is given in Table 2 below.

In this and subsequent Examples that ethoxylated alcohols supplied under the trade mark SYNPERONIC are used herein are all linear $C_{13}$–$C_{15}$ alcohols whose ethylene oxide content is indicated as the number after the suffix "A".

The abbreviations used for the species in this and subsequent Examples is indicated in Table I.

TABLE I

| Species | | Number of days after treatment assessment made |
|---|---|---|
| AGGRRE | Elmus Repens | 15 |
| SORHA | Sorghum halepense | 14 |
| CHEAL | Chenopodium album | 13 |
| ABUTH | Abutilon theophrasti | 14 |

EXAMPLE 2

The procedure of Example 1 was repeated using 0.25% w/v tank-mixed adjuvant system containing equal weights of SYNPERONIC A16 and the ethoxylated alkylglucoside of formula (ii) commercially available as GLUCAN E-20 at a strength of 10% w/w. The ED 90 values are presented in Table 2.

COMPARISON 1

The procedure of Example 1 was repeated using 0.25% w/v tank-mixed SYNPERONIC A16 alone. The ED 90 values are presented in Table 2.

TABLE 2

ED 90 VALUES

| | SPECIES | | | |
|---|---|---|---|---|
| EXAMPLE | CHEAL | ABUTH | SORHA | AGREE |
| 1 | 408 | 696 | 215 | 406 |
| 2 | 655 | 755 | 540 | 1083 |
| Comparison | 1658 | 1022 | 810 | 2067 |

EXAMPLE 3

This Example illustrates the herbicidal activity and rainfastness of compositions of the present invention.

To an aqueous solution containing 720 g/l of the trimethylsulphonium salt of N-phosphonomethylglycine was added 0.125% on a volume per volume basis of SYNPERONIC A16 and 0.125% on a volume per volume basis of the active component of GLUCQUAT 125.

Corresponding comparison concentrates were prepared in which the adjuvant system containing both GLUCQUAT 125 and SYNPERONIC A16 was replaced by (a) 0.25% on a volume per volume basis of only GLUCQUAT 125 (Comparison 2) (b) by 0.25% on a volume per volume basis of only SYNPERONIC A16 (Comparison 3) and (c) 0.25% on a volume by volume basis of a conventional alkylpolyglycoside surfactant commercially available from Imperial Chemical Industries as AL2042 (Comparison 4)

Required aliquots of each formulation were diluted to provide an application corresponding to 0.25 lb of active ingredient per acre (280 g/ha), 0.5 lb active ingredient per acre (560 g/ha) and 01.0 lb active ingredient per acre (1120 g/ha) respectively. This was sprayed in three replicates onto young pot plants. Half the plants from each treatment were then returned to warm or temperate glasshouse environments as appropriate for optimal growth. The remaining plants were first subjected to simulated rain three hours after the treatments were applied. The plants were then returned to the glasshouse.

Activity (damage to plants) was assessed 28 days after treatment by comparison with untreated plants on a 0–100% scale, where 0% is no damage and 100% is complete kill. The species treated are indicated in Table 3.

TABLE 3

*Ipomonea hederaca*
*Digitaria sanguinalis*
*Sida spinosa*
*Abutilon theophrasti*
*Cyperus esculentus*
*Glycine max*

The results are given in Table 4 in which the weed control is expressed as an average value over the above species.

TABLE 4

| Sample | Average Weed Control With No Rain | | | Average Weed Control with Simulated Rain | | |
|---|---|---|---|---|---|---|
|  | 0.25 lb ai/a | 0.5 lb ai/a | 1.0 lb ai/a | 0.25 lb ai/a | 0.5 lb ai/a | 1.0 lb ai/a |
| Example 3 | 60 | 83 | 96 | 44 | 72 | 86 |
| Comparison 2 | 63 | 79 | 93 | 41 | 60 | 80 |
| Comparison 3 | 57 | 76 | 92 | 41 | 65 | 76 |
| Comparison 4 | 61 | 76 | 89 | 38 | 64 | 79 |

We claim:

1. A glyphosate composition comprising (i) N-phosphonomethylglycine or an agriculturally acceptable salt thereof, (ii) a alkylglycoside surfactant of formula (I)

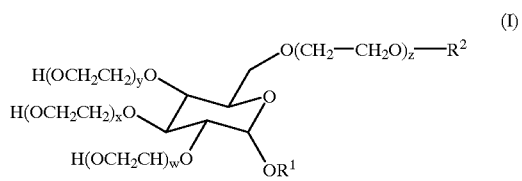

(I)

wherein $R^1$ represents a C1 to C8 alkyl group, the sum of w+x+y+z is from 4 to 40 and $R^2$ is hydrogen or a C1 to C6 alkyl group or a group of formula $—R^3—N^{(+)}R^4R^5R^6\ X^-$ wherein $R^3$ is a C1 to C6 alkylene group optionally substituted with hydroxy, $R^4$, $R^5$ and $R^6$ are each alkyl groups wherein the total number of carbon atoms in $R^4$, $R^5$ and $R^6$ is from 6 to 25 and $X^{-0}$ is an agrochemically acceptable anion and (iii) an ethoxylated alcohol.

2. A composition according to claim 1 wherein $R^1$ represents a C1 to C4 alkyl group and the sum of w+x+y+z is from 4 to 25.

3. A composition according to claim 1 wherein $R^1$ is methyl, $R^2$ is hydrogen and the sum of w+x+y+z is from 10 to 20.

4. A composition according to claim 1 wherein $R^2$ is $$—CH_2—CHOH—CH_2—N^{(+)}R^4R^5R^6\ X^-$$

wherein the total number of carbon atoms in $R^4$, $R^5$ and $R^6$ is from 6 to 25 and $R^4$ and $R^5$ are methyl or ethyl.

5. A composition according to claim 1 wherein the ethoxylated alcohol is obtained by ethoxylation of a linear or branched chain aliphatic mono alcohol having a chain length of from 8 to 20 carbon atoms or a mixture of such alcohols and has a mean degree of ethoxylation of from 2 to 50 moles of ethylene oxide per mole of alcohol.

6. A composition according to claim 5 wherein the ethoxylated alcohol is obtained by ethoxylation of a linear or branched chain aliphatic mono alcohol having a chain length of from 10 to 18 carbon atoms or a mixture of such alcohols and has a mean degree of ethoxylation of from 11 to 18 moles of ethylene oxide per mole of alcohol.

7. A composition according to claim 1 wherein the proportion of alkylglycoside is from 1 part by weight of alkylglycoside per 5 parts by weight of ethoxylated alcohol to 8 parts by weight of alkylglycoside per 1 part by weight of ethoxylated alcohol.

8. A composition according to claim 7 wherein the proportion of alkylglycoside is from 0.5 parts by weight of alkylglycoside per 1 part by weight of ethoxylated alcohol to 8 parts by weight of alkylglycoside per 1 part by weight of ethoxylated alcohol.

9. A composition according to claim 1 which is a herbicidal concentrate wherein there is used a water-soluble salt of N-phosphonomethylglycine and the concentration of the N-phosphonomethylglycine salt is greater than 210 g/l based on glyphosate acid.

10. A composition according to claim 1 wherein the proportion by weight of the total adjuvant system, being the alkylglycoside, ethoxylated alcohol and additional surfactant, if used, to the N-phosphonomethylglycine or the agriculturally acceptable salt thereof is from 3:1 to 1:3.

11. A process of severely damaging or killing unwanted plants, and more particularly a process of providing enhanced activity or enhanced rainfastness which comprises applying to the plants a herbicidally effective amount of a composition according to claim 1.

* * * * *